US006645917B2

(12) United States Patent
Mahajan et al.

(10) Patent No.: US 6,645,917 B2
(45) Date of Patent: Nov. 11, 2003

(54) COMPOSITION FOR HYBRID SEED PRODUCTION, PROCESS FOR THE PREPARATION OF SUCH COMPOSITION AND USE THEREOF

(75) Inventors: Vinay Mahajan, Haryana (IN); Subrahamnium Nagarajan, Haryana (IN); Vishnu Hari Deshpande, Maharashtra (IN); Ramesh Ganesh Kelkar, Maharashtra (IN); Rajgopal Jagannath LaHoti, Maharashtra (IN); Sadyandy Ramlingam, Maharashtra (IN); Vivek Jagannathrao Bulbule, Maharashtra (IN)

(73) Assignees: Council of Scientific and Industrial Research, Rafi Marg (IN); Indian Council of Agricultural Research, Krishi Bhavan (IN)

( * ) Notice: Subject to any disclaimer, the term of this patent is extended or adjusted under 35 U.S.C. 154(b) by 0 days.

(21) Appl. No.: 10/113,215

(22) Filed: Mar. 28, 2002

(65) Prior Publication Data

US 2003/0192070 A1 Oct. 9, 2003

(51) Int. Cl.[7] .................. A01N 43/58; A01N 43/60; C07D 237/00
(52) U.S. Cl. .................. 504/238; 504/136; 504/137; 544/239; 514/247; 514/183
(58) Field of Search .................. 514/247, 183; 544/239, 224; 504/238, 136, 137

(56) References Cited

U.S. PATENT DOCUMENTS

| | | | | |
|---|---|---|---|---|
| 4,345,934 A | * | 8/1982 | Fujimoto | 71/92 |
| 4,661,145 A | * | 4/1987 | Fujimoto | 71/92 |
| 6,187,920 B1 | * | 2/2001 | Komori | 544/239 |
| 6,376,427 B1 | * | 4/2002 | Mito | 504/137 |
| 6,551,963 B1 | * | 4/2003 | Linker et al. | 504/238 |

OTHER PUBLICATIONS

Goasdoue e t al. (DN 120:4756, CAPLUS, abstract of Phytochemistry (1993), 34(2), 375–80).*

DN 104:223734, CAPLUS, abstract of Federal Register (1986), 51(63), 11306–7 Apr. 2, 1986.*

A.A. Pickett, *Fortschritte der Pflanzenzuchtung, Advances in Plant Breeding*, 1993, 122–132.

V. Mahajan et al., *PINSA*, 1998, B64, No. 1 pp. 51–58.

V. Mahajan et al., *Current Science*, 78(3):235–237.

V. Mahajan et al., *Wheat*, 1998, 101–106.

JV Zadoks et al., *Weed Research*, 1974, 14(6):415–421.

* cited by examiner

*Primary Examiner*—Sabiha Qazi
(74) *Attorney, Agent, or Firm*—Morgan & Finnegan, LLP

(57) ABSTRACT

The present invention relates to a novel composition comprising a mixture of potassium 1-[4-chlorophenyl]-1,4 dihydro-6-methyl-4-oxopyridazine-3-carboxylate is in the range of from 1 ppm to 300 ppm and potassium 1-[4-fluoro-3-chlorophenyl]-1,4 dihydro-6-methyl-4-oxopyridazine-3-carboxylate and a non-ionic surfactant for hybrid seed production. The composition of the invention enhances functional male sterility with improved female fertility facilitating commercial production of hybrid seed of wheat and other crops, cereals in particular, across a range of environments.

13 Claims, No Drawings

COMPOSITION FOR HYBRID SEED PRODUCTION, PROCESS FOR THE PREPARATION OF SUCH COMPOSITION AND USE THEREOF

FIELD OF THE INVENTION

The present invention relates to a composition for hybrid seed production. More particularly the present invention also relates- to a composition useful for improving female fertility and seed setting in plants. The composition of the present invention is useful for production of hybrid seed in crop plants such as wheat.

BACKGROUND OF THE INVENTION

Capability of certain classes of chemicals viz. pyridazines, 4-pyridionones, pyrrole carboxylates, 5-chlorocaboxylic acids to effect such changes is know in the literature. Certain compounds designated as DPX 3778, Hybrex, LY 195259, Mendok, RH 2956, RH 4667, RH 5148 and WL 84811 are few of the examples of such compounds. (Pickett A A 1993. In 'Advances in plant Breeding' 15, Paul Parey Scientific Publisher, Berlin, pp 122–132). However, these chemicals also affect female sterility resulting in lower seed setting and seed germination.

The prior art compositions/compounds suffer from several disadvantages in use such as resulting in some growth inhibition, severe plant damage, small seeds, inhibition of growth and flowering, leaf burn, shorter plant, etc. In view of the above limitations it is necessary to provide chemicals and their combinations, which may provide foolproof male sterility with better female fertility for commercial seed production of hybrid seed. Although the study and the research was carried out on wheat in the present description, the involved compositions are not only applicable to the wheat plant but are also to other angiosperm crops as rice, maize, jowar, bajra, etc.

Based on the mode of pollination, the crop plants are classified into three broad groups namely, self-pollinated, cross pollinated and often cross pollinated. Exploitation of heterosis through hybrid breeding is common in cross pollinated and often cross pollinated as their floral structure facilitate natural out crossing. Wheat is a self-pollinated cleistogamy flower wherein flower open only after anther had released their pollen load inside the floret. The success of hybrid breeding depends upon how economically hybrid seed can be produced specially in self-pollinated crops. The three plant breeding methodologies known to develop hybrids are genetic, cytoplasmic and cytoplasmic-genetic. The success story of hybrid rice is a suitable example for a cytoplasmic male sterility (CMS) System.

During the process of evolution the A, B and D genomes of Triticum spp and other related species had combined to form the present hexaploid wheat that man effectively domesticated and commercially grew for food as a cereal crop. These genomes have an ability to survive independently in nature. This hexaploid nature of wheat could be a probable reason that restricts the use of CMS system of hybrid seed production. The initiation of global efforts to use CMS system in early fifties using different sources of male sterility as a mode of hybrid wheat seed production, faced three main limitations viz. A. Instant ability of male sterile line over years; B. Lack of complete restoration; C. Limited use of parental lines because of the tedious and time consuming procedure to develop. A line (male sterile line); B line (maintainer) and identifying good R line (restorer).

Due to these difficulties, several organizations in the early 1970's shifted their efforts to the use of chemicals, which can act like gametocides or pollen suppressant. These chemicals were referred to as "Chemical Hybridizing Agent" (CHA) and a number of CHAs were evaluated. In last 15 years progress has been made for commercial exploitation of hybrid wheat through the use of CHAs (see table 1). Table 1 given below shows the results of investigations made using various chemicals as chemical hybridizing agents (CHA's).

TABLE 1

Chemicals investigated for use as CHA s in wheat

| Chemicals Hybridizing Agents | Sterility (optimum treatment) | | Remarks | Company (where available) |
|---|---|---|---|---|
| | Male | Female | | |
| Dalapon | Partial | Severe | Severe plant damage | Dow Chemicals |
| DPX 3778 | High | Sight | Shorter plant, leaf burn, delayed flowering, toxic residues in seed | El du Pont de Nemours |
| Estrone | Poor | Ovule | Plant damage | — |
| Ethephon (Ethrel) | High | Significant | Height and seed size reduced, late tillers fertile, dose cv specific increased plant height, chlorosis risk of damage | Amchem Products |
| Gibberellic acid | Poor | Nil | Increased plant height, chlorosis | — |
| Hybrex | High | Slight | Risk of damage | Rohm and Haas |
| LY 195259 | High | Nil | Application time critical | Lilly Research |
| Maleic Hydrazide | Partial | Severe | Severe plant damage, late maturity | — |
| Mendok (FW 450) | Poor | Significant | Severe plant damage, small seed | Rohm and Haas |
| RH-531 | High | Significant | Inhibit veg. Growth and flowering | Rohm and Haas |
| RH-532 | High | Significant | Inhibit veg. Growth and flowering | Rohm and Haas |
| RH-2956 | High | Slight | Some growth inhibition | Rohm and Haas |
| RH-4667 | High | Slight | Some growth inhibition | Rohm and Haas |
| RH-5148 | High | Slight | Risk of damage | Rohm and Haas |
| WL 84811 | Nearly complete | Very slight | Toxic residues in F1 seed | Shell chemicals |

Since early eighties a number of CHA molecules were evaluated against wheat (see Table 1) that had variable effect on male and female sterility and some of them affected the plant morphology and caused seed shriveling.

These chemicals differ with respect of female fertility, duration and dose specificity, genotypic and tissue specificity, developmental stage, physiological state, chronic spray, fertility impairment, detrimental side effect and phyto-toxicity. (Mahajan V, Nagarajan S 1997. PINSA B64 No. 1 pp 51–58).

In spite of these difficulties a suitable CHA may have a public acceptance if it is an easy, economical and reliable method for inducing selective male sterility over diverse environments. The CHA can also become an effective tool for emasculation in a traditional breeding programme.

In 1997–98, both Ch 9701 and Ch9832 were evaluated over different genotypes (Mahajan V, Nagarajan S, Deshpande V H and Kelkar R G 2000. Current Science 78 (3): 235–237). At a minimum effective dose for complete male sterility, the female sterility and seed shriveling was higher in CH9701 while seed setting was numerically higher in CH9832. The seed germination was comparable (Table 2).

TABLE 2

Performance of CHA exhibition complete male sterility at 7–8 mm of spike length for important characters

| Chemical Hybridizing Agent | Variety | Effective dose | Female sterility | Max. seed shriveling (Scale 1–5) | Seed setting | Germination (%) |
|---|---|---|---|---|---|---|
| CH9701 | WH542 | 250 | 90.7 | 2 | 56.7 | 85 |
|  | PBW343 | 500 | 88.3 | 3 | 20.0 | 95 |
| CH9832 | WH542 | 500 | 10.7 | 2 | 65.5 | 65 |
|  | PBW343 | 500 | 40.2 | 2 | 49.0 | 90 |

Source : Mahajan et. Al. 2000

Thus all previous research on CHA was not successful in identifying a combination of chemicals which may provide a functional hybrid seed production method in wheat with higher female fertility, seed setting, seed yields, seed viability and versatility over a range of genotypes and environments.

OBJECTS OF THE INVENTION

The main object of the present invention is to provide a novel composition for hybrid seed production.

Another object of the present invention is to provide a composition to improve female fertility.

Still another object of the present invention is to provide a composition useful for increasing seed setting.

Yet another object of the present invention is its effectiveness over a range of genotypes and environments.

SUMMARY OF THE INVENTION

Accordingly the present invention provides a composition for hybrid seed production, which comprises a synergistic mixture of potassium 1-[4-chlorophenyl]-1,4 dihydro-6-methyl-4-oxopyridazine-3-carboxylate of the formula 1

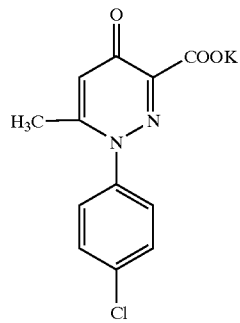

(1)

and potassium 1-[4-fluoro, 3-chlorophenyl]-1,4 dihydro6-methyl-4-oxopyridazine-3-carboxylate of the formula 2

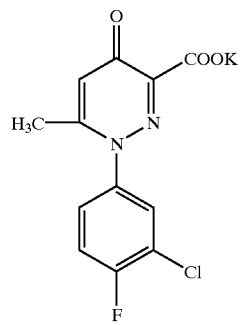

(2)

In one embodiment of the present invention, the compounds of the formula 1 and 2 are taken in a combined dose of up to 1000 ppm along with a non-ionic surfacant.

In one embodiment of the invention the concentration of potassium 1-[4-chlorophenyl]-1,4 dihydro-6-methyl-4-oxopyridazine-3-carboxylate is in the range of from 1 ppm to 300ppm.

In another embodiment of the invention, the concentration of potassium 1-[4-fluoro-3-chlorophenyl]-1,4 dihydro-6-methyl-4-oxopyridazine-3-carboxylate is in the range of 700 ppm to 999 ppm.

In still another embodiment of the invention, the non-ionic surfactant is selected from the group consisting of polyoxyethylene sorbitan monoaurate, polyoxyethylene sorbitan monopalmitate, polyoxyethylene sorbitan monooleate, polyoxyethylene sorbitan trioleate and any combination thereof.

In yet another embodiment of the invention, the concentration of the non-ionic surfactant is in the range of 1–10% of an aqueous solution prepared from a mixture of compounds of formula 1 and 2.

The present invention also relates to a process for the preparation of a composition for hybrid seed production, comprising a synergistic mixture of potassium 1-[4-chlorophenyl]-1,4 dihydro-6-methyl-4-oxopyridazine-3-carboxylate of the formula 1

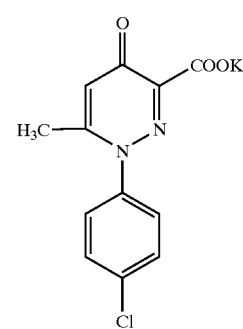

(1)

and potassium 1-[4-fluoro, 3-chlorophenyl]-1,4 dihydro-6-methyl-4-oxopyridazine-3-carboxylate of the formula 2

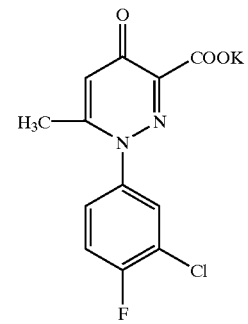

(2)

said process comprising mixing said compounds of formula 1 and 2 in a non-ionic surfactant such that the combined dosage of the compounds of formula 1 and 2 is up to 1000 ppm.

In one embodiment of the invention the concentration of potassium 1-[4-chlorophenyl]-1,4 dihydro-6-methyl-4-oxopyridazine-3-carboxylate is in the range of from 1 ppm to 300ppm.

In another embodiment of the invention, the concentration of potassium 1-[4-fluoro-3-chlorophenyl]-1,4 dihydro-6-methyl-4-oxopyridazine-3-carboxylate is in the range of 700 ppm to 999 ppm.

In still another embodiment of the invention, the non-ionic surfactant is selected from the group consisting of polyoxyethylene sorbitan monoaurate, polyoxyethylene sorbitan monopalmitate, polyoxyethylene sorbitan monooleate, polyoxyethylene sorbitan trioleate and any combination thereof.

In yet another embodiment of the invention, the concentration of the non-ionic surfactant is in the range of 1–10% of an aqueous solution prepared from a mixture of compounds of formula 1 and 2.

The present invention also relates to the use of a composition comprising a mixture of compounds of formula 1 and 2 above in an non-ionic surfactant for hybrid seed production.

DETAILED DESCRIPTION OF THE INVENTION

The composition of the invention enhances functional male sterility with improved female fertility facilitating commercial production of hybrid seed of wheat and other crops, cereals in particular, across a range of environments.

EXAMPLE

The effects of the composition with varied concentration of compound 1 and 2 were evaluated for two crops years. The aqueous solution of the compositions were sprayed on the wheat plants when the Spike length of 7–12 mm. i.e. growth of 20–22 of Zadoks scale, reached between 40–50 days after germination. The results are summarized in Table-3.

In a future of the present invention the calculation of male/female sterility is based on number of seeds and is done as per formula given below:

Male Sterility (%)=(Untreated Control−Bagged Spikes×100/Untreated Control

Female Sterility (%)=(Untreated Control−Bagged Spikes)×100/Untreated Control (Mahajan V, Singh K, Kelkar R. G. 2000. In "Wheat Research Needs Beyond 2000AD (Eds. Nagarjana S, Singh G and Tyagi B S) Narosa Publishing House, New Delhi pp 101–106.)

SCIENTIFIC EXPLANATION: Compound of formula 1, (designated hereinafter as CH9701) was found to cause high female sterility, low seed set along with damage to florets. Compound of formula 2 (designated hereinafter as CH9832) was found to cause low female sterility, no damage to florets thereby low seed set due to naturally closed structure of wheat florets. Both the chemicals exhibited complete male sterility. In the present invention, it was surprisingly found that when the two compounds of formula 1 and 2 respectively were combined, along with a non-ionic surfactant, higher female fertility and higher seed set and stability was achieved across major environments. This composition facilitates a regulated artifact because little damage to floret permitting easy way to outside pollen to ovary thereby leading to improved seed setting.

Method for Hybrid Seed Production in Wheat

Planting of male/female lines: An ideal time of planting of hybrid seed production is from last week of November to the first week of December in North-Western Plains Zone of India. The male and female were grown alternatively in 2:4/3:6 ratios and routine agronomic practices were followed.

Preparation of Chemical

The compounds CH9701 and Ch9832 were combined in different formulations. The proportion of CH9701 can be 30% or below in the formulation while the proportion of CH9832 can be 70% or above, depending upon genotype, date of planting and growth stage. A sticking-cum-spreading agents viz. TWEEN 20/TWEEN 80 etc. is mixed in the solution in small quantity (2–5 ml/liter) and stirred properly.

TABLE 3

Effect of spray of chemicals in combinations over individual molecules

| Treatment | Composition with concentration of 1 & 2 (ppm) | Seeds/spike unbagged | Female sterility (%) | Seed grade (A–E* & %) | Germination (%) Expected # | Seed produced (g) | Seed produced (% to check) |
|---|---|---|---|---|---|---|---|
| 1 | 800 + 200 | 37.8 | 15.0 | B80C20 | 70.0 | 28.0 | 66.2 |
| 2 | 700 + 300 | 40.7 | 8.5 | A80B20 | 87.00 | 37.4 | 88.4 |
| 3 | 600 + 400 | 16.2 | 63.6 | B80C20 | 70.0 | 12.0 | — |
| 4 | 500 + 500 | 22.5 | 49.4 | A30C70 | 62.0 | 14.3 | — |
| 5. | 400 + 600 | 10.7 | 76.0 | B20C80 | 55.0 | 6.0 | — |
| 6. | 300 + 700 | 7.6 | 82.9 | A80B20 | 87.0 | 7.0 | — |
| 7 | 200 + 800 | 13.5 | 44.2 | A80b20 | 87.0 | 12.4 | — |
| 8. | 1000 + 0 | 31.0 | 30.3 | A20b80 | 78.0 | 25.7 | 60.7 |
| 9. | 0 + 1000 | 24.8 | 46.1 | A90b10 | 88.5 | 23.2 | 54.8 |
|   | Check | 44.5 | — | A100 | 90.0 | 42.3 | 100.0 |

Note
*A: Normal seed and E: Highly shriveled seed
To calculate expected seed germination A, B, C, D, and E (visual scoring) equated as 0.90, 0.75, 0.50, 0.25 and 0.05 respectively.

Spray of Chemical Combination

The chemical formulation can be used at a rate of 1.8 kg/ha or below (following male: female ratio of 1:2) depending upon genotypes used, date of planting and growth stage. The female lines were sprayed with the chemical combination at the appropriate growth stage and concentration. The spike of 7–12 mm i.e. growth stage 20–22 of Zadoks scale (Zadoks J V, Chang T T and Konzak C F 1974. Weed Research 14: 415421) was ideal for generating effective male sterility in spring wheat. This stage is reached between 40–50 days after germination at optimum time of sowing in most of the genotypes. The date of spray varied depending upon the genotype used. A high volume spray pump may be used so as to cover the complete female plant.

Post Spray Operation in Hybrid Seed Production

On emergence of spike the floret open due to sterility induced by CHA formulation. At this stage the ovary is to be protected from insects like aphid (*Sitobion avanae*) and shoot fly (*Alherigona naqvi*) that needs to be controlled using dimethoate (Trade name: Rogar ) at 150 g a.i./ha and cypermedhrin at 60 g ai/ha, respectively. A precautionary spray of "Rogar" before spike emergence (Stage: 58 of Zadoks scale) help in reducing the initial build-up of the insect population.

The wheat genotypes vary with respect to pollen extrusion from the wheat floret. In addition wheat pollen do not have an efficient natural mechanism of pollen dispersal that help it to reach the ovary of another plant. Studies have shown that wheat pollen cannot go beyond 5 m even in the absence of any natural/artificial barrier. The two times (forenoon and evening) shaking of male parent by rope pulling across male parent help in improving the seed setting in female parents. A rope is used for shaking male parents as followed in hybrid rice (self pollinated) seed production. The rope can be moved from one corner to another so that pollen are lifted along with the rope by shaking and carried to another nearby female plant. This method may achieve hybrid seed yield up to 0.35 kg/m² of female plant area.

Conclusion:

A number of chemicals are known in literature which can cause partial to complete male sterility but it is also associated with increased female sterility, lower seed germination, reduced seed size, inhibit plant growth and flowering and other plant damages. The commercial use of CHAs is possible only if it can be used to produce more viable hybrid seed in good quantity with least effect on other plant characters. The advantage of proposed invention is capability to achieve complete male sterility with high female fertility and normal seed setting facilitating commercial production of hybrid seed of wheat and other crops across a range of environments.

The Main Advantages of the Present Invention are

1. Improved seed setting in sprayed plants.
2. Lesser female sterility in sprayed plants.
3. Complete male sterility in wheat plants.

We claim:

1. A composition for hybrid seed production, comprising a mixture of potassium 1-[4-chlorophenyl]-1,4-dihydro-6-methyl-4-oxopyriazine-3-carboxylate of formula 1

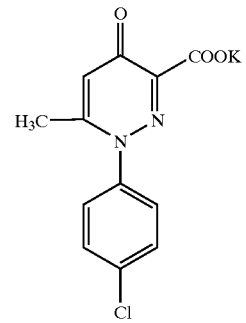

and potassium 1-[4-fluoro-3-chlorophenyl]-1,4-dihydro-6-methyl-4-oxopyriazine-3-carboxylate of formula 2

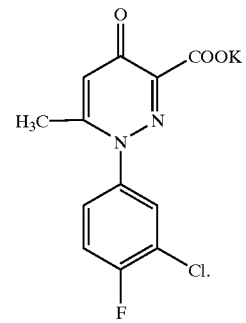

2. A composition as claimed in claim 1 wherein the compounds of formula 1 and 2 are taken in a combined dose of up to 1000 ppm along with a non-ionic surfactant.

3. A composition as claimed in claim 1 wherein the concentration of compound of formula 1 is in the range of from 1 ppm to 300 ppm.

4. A composition as claimed in claim 1 wherein the concentration of compound of formula 2 is in the range of from 700 ppm to 999 ppm.

5. A composition as claimed in claim 1 wherein the non-ionic surfactant is selected from the group consisting of polyoxyethylene sorbitan monoaurate, polyoxyethylene sorbitan monopalmitate, polyoxyethylene sorbitan monooleate, polyoxyethylene sorbitan trioleate and any combination thereof.

6. A composition as claimed in claim 1 wherein the concentration of the non-ionic surfactant is in the range of 1–10% of an aqueous solution prepared from compounds of formula 1 and 2.

7. A process for the preparation of a composition a mixture of potassium 1-[4-chlorophenyl]-1,4-dihydro-6-methyl-4-oxopyriazine-3-carboxylate of formula 1

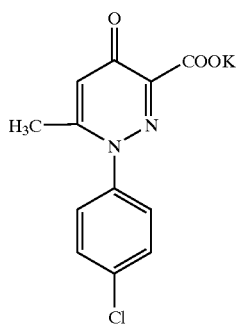

and potassium 1-[4-fluoro-3-chlorophenyl]-1,4-dihydro-6-methyl-4-oxopyriazine-3-carboxylate of the formula 2

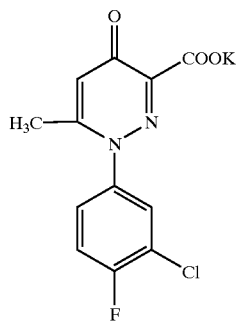

said process comprising mixing said compounds of formula 1 and 2 in a non-ionic surfactant such that the combined dosage of the compounds of formula 1 and 2 is up to 1000 ppm.

8. A process as claimed in claim 7 wherein the concentration of 1-[4-chlorophenyl]-1,4-dihydro-6-methyl-4-oxopyriazine-3-carboxylate is in the range of from 1 ppm to 300 ppm.

9. A process as claimed in claim 7 wherein the concentration of 1-[4-fluoro-3-chlorophenyl]-1,4-dihydro-6-methyl-4-oxopyriazine-3-carboxylate is in the range of from 300 ppm to 999 ppm.

10. A process as claimed in claim 7 wherein the non-ionic surfactant is selected from the group consisting of polyoxyethylene sorbitan monoaurate, polyoxyethylene sorbitan monopalmitate, polyoxyethylene sorbitan monooleate, polyoxyethylene sorbitan trioleate and any combination thereof.

11. A process as claimed in claim 7 wherein the concentration of the non-ionic surfactant is in the range of 1–10% of an aqueous solution prepared from compounds of formula 1 and 2.

12. A method for hybrid seed production in a plant by applying a composition comprising a mixture of 1-[4-chlorophenyl-]1,4-dihydro-6-methyl4-oxopyriazine-3-carboxylate and 1-[4-fluoro-3-chlorophenyl]-1,4-dihydro-6-methyl-4-oxopyriazine-3-carboxylate in an non-ionic surfactant to a plant.

13. A process as claimed in claim 12 wherein the plant is wheat.

* * * * *